(12) United States Patent
Krebber et al.

(10) Patent No.: US 9,791,269 B2
(45) Date of Patent: Oct. 17, 2017

(54) DENT MIRROR

(71) Applicants: Jutta Krebber, Cape Coral, FL (US);
Kattkus Klaus, Cape Coral, FL (US)

(72) Inventors: Jutta Krebber, Cape Coral, FL (US);
Kattkus Klaus, Cape Coral, FL (US)

( * ) Notice: Subject to any disclaimer, the term of this patent is extended or adjusted under 35 U.S.C. 154(b) by 198 days.

(21) Appl. No.: 14/472,939

(22) Filed: Aug. 29, 2014

(65) Prior Publication Data

US 2016/0061744 A1  Mar. 3, 2016

(51) Int. Cl.
*G01B 11/30* (2006.01)
*G01N 21/88* (2006.01)

(52) U.S. Cl.
CPC ....... *G01B 11/306* (2013.01); *G01N 21/8803* (2013.01); *G01N 2201/068* (2013.01); *G01N 2201/0616* (2013.01)

(58) Field of Classification Search
USPC .......................................................... 235/449
See application file for complete search history.

(56) References Cited

U.S. PATENT DOCUMENTS

| | | | |
|---|---|---|---|
| D210,543 S * | 3/1968 | Nakayama | 473/513 |
| 4,084,033 A | 4/1978 | Drelich | |
| 4,628,545 A | 12/1986 | Metzler | |
| 4,774,778 A | 10/1988 | Williams | |
| 5,849,358 A | 12/1998 | Le Riche et al. | |
| 5,851,592 A | 12/1998 | Le Riche et al. | |
| 5,863,330 A | 1/1999 | Alain Le Riche et al. | |
| 5,868,838 A | 2/1999 | Le Riche et al. | |
| 5,916,630 A | 6/1999 | Le Riche et al. | |
| 5,958,135 A | 9/1999 | Pierre | |
| 5,972,113 A | 10/1999 | Le Riche et al. | |
| 6,040,006 A | 3/2000 | Le Riche et al. | |
| 6,059,915 A | 5/2000 | Lightle et al. | |
| 6,074,704 A | 6/2000 | Le Riche et al. | |
| 6,153,128 A | 11/2000 | Lightle et al. | |
| 6,261,670 B1 | 7/2001 | Hakomori et al. | |
| 6,270,832 B2 | 8/2001 | Honda et al. | |
| 6,373,573 B1 | 4/2002 | Jung et al. | |
| 6,416,914 B1 | 7/2002 | Nakamura et al. | |
| 6,458,505 B2 | 10/2002 | Ito | |
| 6,476,726 B1 | 11/2002 | Pederson | |
| 6,482,489 B1 | 11/2002 | Otaki et al. | |
| 6,514,662 B2 | 2/2003 | Ito | |
| 6,517,900 B1 | 2/2003 | Pierre | |
| 6,548,239 B2 | 4/2003 | Goto | |

(Continued)

*Primary Examiner* — Michael G Lee
*Assistant Examiner* — David Tardif
(74) *Attorney, Agent, or Firm* — Mark Terry

(57) ABSTRACT

The present invention comprises a surface to maximize the viewing of an impression in a vehicle body. This may comprise a fabric which has at least one dark colored stripe parallel to at least one light colored stripe; a compressible frame across which the said fabric is affixed, where when the frame is uncompressed the fabric is stretched taut across the frame and where the frame is compressed the fabric is slack across the frame; and a handle on the frame where a user can hold the frame and not interfere with the fabric affixed to said frame. When a user is holding the handle of the frame at an angle between 0° and 180°, the user can reflect radiant energy through said fabric onto the vehicle body and create a whorl reflection pattern on the impression to maximize viewing of said impression by the user.

7 Claims, 4 Drawing Sheets

(56) References Cited

U.S. PATENT DOCUMENTS

| | | |
|---|---|---|
| 6,548,240 B2 | 4/2003 | Yamaguchi |
| 6,590,343 B2 | 7/2003 | Pederson |
| 6,610,469 B2 | 8/2003 | Ishihara |
| 6,645,714 B2 | 11/2003 | Oya et al. |
| 6,671,100 B1 | 12/2003 | McRuer |
| 6,699,653 B2 | 3/2004 | Goto |
| 6,707,389 B2 | 3/2004 | Pederson |
| 6,787,298 B2 | 9/2004 | Goto et al. |
| 6,800,430 B2 | 10/2004 | Kyota et al. |
| 6,808,587 B2 | 10/2004 | Bohm et al. |
| 6,824,962 B2 | 11/2004 | Oikawa |
| 6,849,149 B2 | 2/2005 | Otaki et al. |
| 6,974,610 B1 | 12/2005 | Koppes |
| 7,046,160 B2 | 5/2006 | Pederson et al. |
| 7,064,674 B2 | 6/2006 | Pederson |
| 7,080,930 B2 | 7/2006 | Pederson |
| 7,153,013 B2 | 12/2006 | Pederson |
| 7,355,467 B2 | 4/2008 | Waldstein et al. |
| 7,827,350 B1 | 11/2010 | Jiang et al. |
| 7,896,858 B2 | 3/2011 | Trennepohl et al. |
| 7,997,102 B2 | 8/2011 | Obadalova |
| 8,068,676 B2 | 11/2011 | Zhang et al. |
| 8,133,341 B2 | 3/2012 | Nealey et al. |
| 8,153,284 B2 | 4/2012 | Kawai |
| 8,169,454 B1 | 5/2012 | Hajjar et al. |
| 8,224,018 B2 | 7/2012 | Rhoads et al. |
| 8,277,592 B2 | 10/2012 | Hoermann et al. |
| 8,343,574 B2 | 1/2013 | Downs et al. |
| 8,435,625 B2 | 5/2013 | Ruehe et al. |
| 8,460,135 B2 | 6/2013 | Guenther et al. |
| 8,609,243 B2 | 12/2013 | Ogasawara et al. |
| 2008/0268205 A1* | 10/2008 | Vogel .................... D04H 1/64 428/156 |

\* cited by examiner

DENT MIRROR

FIELD OF THE INVENTION

The present invention relates to a surface to maximize the viewing of an impression, which may also be known as a dent, in a vehicle body, to assist with determination of damage for an insurance claim purpose.

BACKGROUND OF THE INVENTION

Insurance claims investigation for vehicle damage has generally included a person, known as a claims adjuster or claim investigator, personally viewing a vehicle for any damage. Commonly, the investigator uses only their eyes and/or a mirror on a handle to view any viewable damage. This method may be problematic, especially where a vehicle has been damaged due to weather phenomena, for example, hail, sleet or snow damage which may produce subtle indentations or waves in the vehicle body, as compared to where a vehicle is damaged due to a crash with another vehicle or inanimate object, for example, such as a light pole, building or the like.

SUMMARY OF THE INVENTION

It is, therefore, an object of the present invention to provide a surface to maximize the viewing of an impression, subtle indentation, and/or wave in a vehicle body. In one exemplary embodiment of the present invention, the surface can further comprise a fabric, a compressible frame across which the fabric is affixed, and a handle on the compressible frame.

An exemplary environment for the present invention can include, but is not limited to, any environment in which viewing impressions, indentations and other surface anomalies on a vehicle would be beneficial.

In one exemplary aspect of the present embodiment, the fabric can have at least one stripe of a dark color parallel to at least one stripe of a light color.

In another exemplary aspect of the present embodiment, the compressible frame across which the fabric is affixed creates the surface.

In a further exemplary aspect, when the compressible frame is uncompressed the fabric is stretched taut across the compressible frame and when the compressible frame is compressed the fabric is slack across the frame.

An additional exemplary aspect of the present embodiment further includes that the handle on the compressible frame is where a user can hold the compressible frame and not interfere with the fabric affixed to said frame.

In yet another exemplary aspect of the present embodiment, when a user is holding the handle of the uncompressed frame at an angle between 0° and 180°, the user can reflect radiant energy through the fabric onto a vehicle body and create a whorl reflection pattern of at least one stripe of a dark color parallel to at least one stripe of a light color on the impression in the vehicle body to maximize viewing of the impression by the user.

The following are additional and/or exemplary aspects of the present surface to maximize the viewing of an impression in a vehicle body, one or more of which can be combined with the basic surface and its elements, as embodied above:
  the fabric has a translucency between 3 deniers and 90 deniers;
  the fabric has a translucency between 20 deniers and 60 deniers;
  the fabric has more than one at least one stripe of a dark color parallel to at least one stripe of a light color creating an alternating pattern;
  the at least one stripe of a dark color has an equal width to the at least one stripe of a light color; and
  the at least one stripe of a dark color has an unequal width to the at least one stripe of a light color.

In another exemplary embodiment of the present invention, a fabric mirror to maximize the viewing of an impression in a vehicle body is provided. In this exemplary embodiment, the fabric mirror can further comprise a woven cloth and a frame to which the woven cloth is affixed.

In an exemplary aspect of the present embodiment, the woven cloth further comprises a pattern of at least one set stripe of a dark color and at least one stripe of a light color.

In another exemplary aspect of the present embodiment, when the woven cloth is affixed to the frame the woven cloth is taut.

In a further exemplary aspect of the present embodiment, when a vehicle body is placed beneath the frame, radiant energy passes through the woven cloth onto the vehicle body and a reflection of the pattern of at least one set stripe of a dark color and at least one stripe of a light color is reflected on the impression in the vehicle body as a whorl pattern to maximize viewing of the impression by a user.

The following are additional and/or exemplary aspects of the present fabric mirror to maximize the viewing of an impression in a vehicle body, one or more of which can be combined with the basic fabric mirror and its elements, as embodied above:
  the woven cloth has a translucency between 3 deniers and 90 deniers;
  the woven cloth has a translucency between 20 deniers and 60 deniers;
  the woven cloth a pattern of more than one stripe of a dark color and more than one stripe of a light color, creating an alternating pattern of stripes;
  the pattern of at least one set stripe of a dark color and at least one stripe of a light color, said stripes are of equal width;
  the pattern of at least one set stripe of a dark color and at least one stripe of a light color, said stripes are of unequal width;
  the frame is a tent or awning structure through which a vehicle comprising the vehicle body can drive;
  a method of using the fabric mirror, comprising:
    locating the vehicle beneath the frame to a location dependent on a direction of radiant energy passing through the woven cloth of the fabric mirror;
    viewing a reflection of the woven cloth of the fabric mirror on the vehicle body created by the directional radiant energy, whereby by the whorl pattern is created by the pattern of at least one set stripe of a dark color and at least one stripe of a light color to maximize; and
    viewing of the impression by a user.

In another exemplary embodiment of the present invention, a method is provided for operating a surface to maximize the viewing of an impression in a vehicle body.

One exemplary step in the present method embodiment comprises uncompressing a frame, across which a fabric is affixed to create the surface.

In this exemplary step in the present embodiment method, when the frame is uncompressed the fabric is stretched taut across the frame and when the frame is compressed the fabric is slack across the frame.

Further in this exemplary step in the present method embodiment, the fabric has an alternating pattern of at least one stripe of a dark color parallel to at least one stripe of a light color;

Another exemplary step in the present method embodiment comprises holding a handle on the frame, where a user can hold the frame and not interfere with the fabric affixed to said frame.

A further exemplary step in the present method embodiment comprises angling the frame so that said fabric has an angle between 0° and 180° in relation to the vehicle body.

Yet another exemplary step in the present method embodiment comprises reflecting radiant energy through the fabric onto the vehicle body thereby creating a whorl reflection pattern of at least one stripe of a dark color parallel to at least one stripe of a light color on the impression in the vehicle body.

Yet still another exemplary step in the present method embodiment comprises viewing of the impression by the user.

The following are additional and/or exemplary steps of the present method, one or more of which can be combined with the basic method and its elements, as embodied above:

the fabric has a translucency between 3 deniers and 90 deniers;

the fabric has a translucency between 20 deniers and 60 deniers;

the fabric has more than one at least one stripe of a dark color parallel to at least one stripe of a light color creating an alternating pattern;

the at least one stripe of a dark color has an equal width to the at least one stripe of a light color; and the at least one stripe of a dark color has an unequal width to the at least one stripe of a light color.

These and other exemplary aspects of the present invention are described herein.

Those skilled in the art will recognize still other aspects of the present invention upon reading and understanding the attached description.

BRIEF DESCRIPTION OF THE DRAWINGS

The present invention is illustrated by way of example, and not in limitation, in the figures of the accompanying drawings. For a better understanding of the present invention and its embodiments, reference will be made to the following detailed description, which is to be read in association with the accompanying drawings.

DETAILED DESCRIPTION OF THE INVENTION

Figure 1:
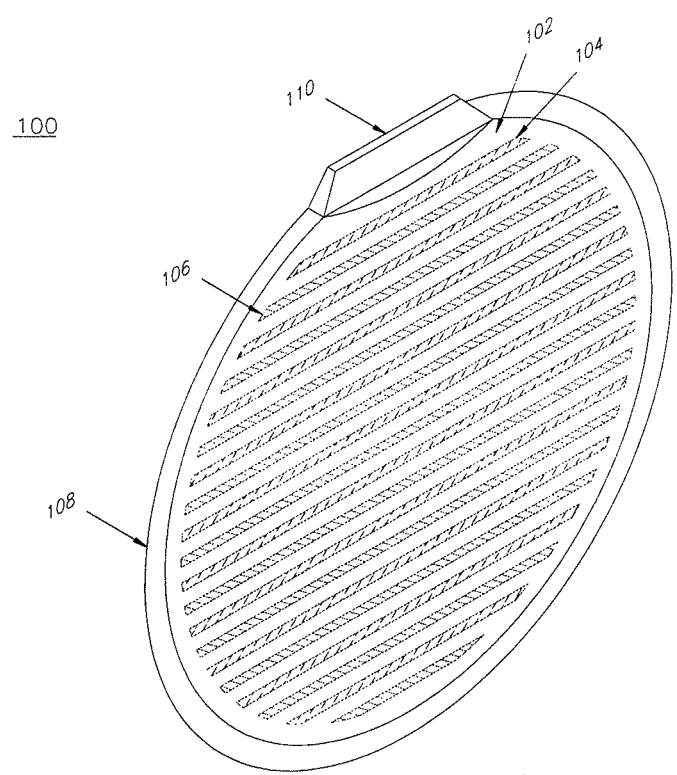
FIG. 1 illustrates one exemplary embodiment of a surface to maximize the viewing of an impression in a vehicle body, generally comprising a fabric, a compressible frame, and a handle.

The present invention will now be described more fully herein after with reference to the accompanying drawings, which form a part hereof, and which show, by way of illustration, specific exemplary embodiments by which the invention may be practiced. This invention may, however, be embodied in many different forms and should not be construed as limited to the exemplary embodiments set forth herein. Rather, these exemplary embodiments are provided so that this disclosure will be thorough and complete, and will fully convey the scope of the invention to those skilled in the art. Among other things, the present invention may be embodied as methods or devices. Accordingly, various exemplary embodiments may take the form of an entirely hardware embodiments, an entirely software embodiment and/or an embodiment combining software and hardware aspects. The following detailed description is, therefore, not to be taken in a limiting sense.

Throughout the specification and claims, the following terms take the meanings explicitly associated herein, unless the context clearly otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The following briefly describes the embodiments of the invention in order to provide a basic understanding of some aspects of the invention. This brief description is not intended as an extensive overview. It is not intended to identify key or critical elements, or to delineate or otherwise narrow the scope. its purpose is merely to present some concepts in a simplified form as a prelude to the more detailed description that is presented later.

The present invention, generally, is directed towards a surface to maximize the viewing of an impression in a vehicle body. This may comprise a fabric which has at least one dark colored stripe parallel to at least one light colored stripe; a compressible frame across which the said fabric is affixed, where when the frame is uncompressed the fabric is stretched taut across the frame and where the frame is compressed the fabric is slack across the frame; and a handle on the frame where a user can hold the frame and not interfere with the fabric affixed to said frame. When a user is holding the handle of the frame at an angle between 0° and 180°, the user can reflect radiant energy through said fabric onto the vehicle body and create a whorl reflection pattern on the impression to maximize viewing of said impression by the user.

FIG. 1 illustrates one exemplary surface 100 for maximizing viewing of an impression in a vehicle body. As shown in FIG. 1, surface 100 further comprises a fabric 102, a compressible frame 108, and a handle 110.

As illustrated in FIG. 1, fabric 102 can have at least one stripe of a dark color 104 and at least one stripe of a light color 106. Fabric 102 can be generally defined as a textile or a cloth material. For example, a textile or cloth is a flexible woven material consisting of a network of natural or artificial fibers often referred to in the industry as thread or yarn. Yarn is produced by spinning raw fibers of wool, flax, cotton, or other material to produce long strands. Textiles are formed by weaving, knitting, crocheting, knotting, or pressing fibers together, for example, such as felt, synthetic or laminated materials, or the like.

Commonly, the words fabric and cloth are used in textile assembly trades, such as tailoring and dressmaking, as synonyms for textile. However, there are subtle differences in these terms in specialized usage. Textile generally refers to any material made of interlacing fibers. Fabric, conversely, generally refers to any material made through weaving, knitting, spreading, crocheting, or bonding that may be used in production of further goods such as garments and the like. Cloth, however, may be used synonymously with fabric but often refers to a finished piece of fabric used for a specific purpose.

Fabric 102, as illustrated in FIG. 1, is shown as a solid fabric, however, it is further contemplated that fabric 102 may also be a textile material, created by interlacing fibers. For example, fabric 102 may be any fabric, cloth or textile-like material that is functionally compatible with the described inventive design, which may be manufactured using any known material production techniques or any unknown material production techniques which are reasonable combinations of known techniques, and which are readily available in the materials industry.

It is further contemplated that fabric 102 have a transparent and/or translucent quality through which any form of radiant energy may pass. Radiance and radiant energy shall be discussed below. Generally, transparency, which may also be called pellucidity or diaphaneity, is the physical property of allowing light to pass through the material without being scattered. On a macroscopic scale, for example, a scale where the dimensions investigated are much, much larger than the wavelength of the photons in question, the photons can be said to follow Snell's Law.

Snell's Law, also known as the Snell-Descartes law and the law of refraction, is a formula used to describe the relationship between the angles of incidence and refraction, when referring to light or other waves passing through a boundary between two different isotropic media, for example, such as water, glass and air. In optics, the law is used in ray tracing to compute the angles of incidence or refraction, and in experimental optics and gemology to find the refractive index of a material. The law is also satisfied in metamaterials, which allow light to be bent "backward" at a negative angle of refraction with a negative refractive index.

Translucency, which may also be called translucence or translucidity, is a super-set of transparency. Generally, translucency allows light to pass through, but does not necessarily follow Snell's law. Where a material is translucent, the photons can be scattered at either of the two interfaces where there is a change in index of refraction, or internally. In one example, a translucent medium allows the transport of light while a transparent medium not only allows the transport of light but allows for image formation. The opposite property of translucency is opacity. Transparent materials appear clear, with the overall appearance of one color, or any combination leading up to a brilliant spectrum of every color.

When light encounters a material, it can interact with it in several different ways. These interactions depend on the wavelength of the light and the nature of the material. Photons interact with an object by some combination of reflection, absorption and transmission. Some materials, such as plate glass and clean water, transmit much of the light that falls on them and reflect little of it; such materials are called optically transparent. Many liquids and aqueous solutions are highly transparent. Absence of structural defects, for example, voids, cracks, tears, and the like, and molecular structure of most liquids are mostly responsible for excellent optical transmission.

Materials which do not transmit light are generally defined as opaque. Many such substances have a chemical composition which includes what are referred to as absorption centers. Many substances are selective in their absorption of white light frequencies. For example, these materials and substances may absorb certain portions of the visible spectrum while reflecting others. The frequencies of the spectrum which are not absorbed are either reflected back or transmitted for our physical observation. This is what gives rise to color. The attenuation of light of all frequencies and wavelengths is due to the combined mechanisms of absorption and scattering.

Translucency and transparency of a fabric is generally measured in deniers. A denier or den is a unit of measure for the linear mass density of fibers. It is defined as the mass in grams per 9000 meters. The denier is based on a natural reference, in one example; a single strand of silk is approximately one denier. A 9000-meter strand of silk weighs about one gram. The term denier comes from the French denier, a coin of small value (worth 1/12 of a sou). In one example, as applied to yarn, a denier was held to be equal in weight to 1/24 of an ounce. The term microdenier is used to describe filaments that weigh less than one gram per 9000 meters. The International System of Units uses the unit kilogram per meter for linear densities and in some contexts the unit "tex" is used instead.

One can distinguish between filament and total measurements in deniers. Both are defined as above but the first only relates to a single filament of fiber—commonly known as denier per filament or DPF—whereas the second relates to a yarn, a spun agglomeration of filaments. Broader terms such as 'fine' may be applied because either the overall yarn is fine or because fibers within this yarn are thin. In one example, seventy-five (75) denier yarn would be considered fine even if it only contains a few fibers, such as thirty, two-denier fibers, but a heavier yarn such as 150 denier is only considered fine if its constituent fibers are individually as thin as one denier. The following relationship applies to straight, uniform filaments: DPF=total denier/quantity of uniform filaments. The denier system of measurement is used on two- and single-filament fibers. Some common calculations are as follows: one denier=1 gram per 9 000 meters=0.111 milligrams per meter.

In practice, measuring 9000 meters is both time-consuming and unrealistic; generally a sample of 900 meters is weighed and the result multiplied by 10 to obtain the denier weight. A few commonly accepted industry standards include, but are not limited to, a fiber being generally considered a microfiber if it is one denier or less; A one denier polyester fiber has a diameter of about ten micrometers; and denier is used as the measure of density of weave in tights and pantyhose, which defines their opacity.

Opacity is commonly categorized into five broad categories by manufacturers in the industry, for example: ultra-sheer, generally defined as 1 to 10 deniers; sheer, generally defined as 10 to 30 deniers; semi opaque, which is generally defined as 30 to 40 deniers; opaque, which is generally defined as 40 to 70 deniers; and thick opaque, which is generally defined as 70 deniers or higher. Additional embodiments of the present invention contemplate fabric 102 having a translucency, in one non-limiting example, between 3 deniers and 90 deniers, and, in another non-limiting example, between 20 deniers and 60 deniers.

As illustrated in FIG. 1, fabric 102 has at least one dark stripe 104 and at least one light stripe 106. As is show in an exemplary fashion in FIG. 1, fabric 102 has a plurality of stripes which run parallel to one another and in an alternating pattern. The embodiment depicted in FIG. 1 illustrates but one of many contemplated embodiments, however, for surface 100. For example, size, dimension, shape, and color of dark stripe 104 and light stripe 106 may take any visually pleasing and/or easily producible form as is reasonably necessary to carry out the purpose and function of surface 200.

For example, different tessellating and/or alternating patterns may include, but are not limited to "awning" stripes, "Bengal" stripes, and "candy" stripes. In one example, awning stripes are the widest sized stripes. These vertical and even stripes are often wider than ¼" and usually consist of solid colored stripes on white. The name derives from the wide stripe pattern found on awning fabrics. Wider stripes tend to be used mostly for casual shirts.

Bengal stripes, on the other hand, may be defined as vertical stripes that are narrower than awning stripes but wider than candy stripes, for example, approximately ¼" in width. Bengal stripes usually consist of solid colored stripes on white. Candy stripes are vertical and even stripes that are wider than pencil stripes but thinner than Bengal stripes. Candy stripes are usually about ⅛" in width and are characterized by solid, bold stripes on white. The name derives from the stripe pattern found on stick candy.

In additional embodiments not illustrated in FIG. 1, fabric 102 can have more than one at least one stripe of a dark color 104 which run parallel to at least one stripe of a light color creating 106, creating an alternating pattern or tessellating pattern. In yet still more embodiments, the at least one stripe of a dark color 104 can have an equal width to the at least one stripe of a light color 106, or optionally the at least one stripe of a dark color 104 can have an unequal width to the at least one stripe of a light color 106.

Surface 100, as further illustrated in FIG. 1, includes a compressible frame 108 across which fabric 102 is affixed to create surface 100. When, for example, compressible frame 108 is uncompressed (as shown in FIG. 1), fabric 102 is stretched taut across compressible frame 108. In another example, when compressible frame 108 is compressed (not shown in FIG. 1), fabric 102 is slack across the frame 108.

As illustrated in FIG. 1, and the above two examples, compressible frame 108 is contemplated to be manufactured from a flexible material which can be easily compressed and uncompressed without failure. Materials which are contemplated include, but are not limited to, metals such as aluminum, copper, and the like; plastics, such as polypropylene and the like, and composite materials which have a high tensile strength and low tactile strength. Additional materials are also considered, however, materials such ceramic, porcelain, and glass are not considered.

Also, compressible frame 108 is illustrated in FIG. 1 as having a circular-like shape. It is contemplated that compressible frame 108 can have any functionally compatible shape, for example, square, triangular, hexagonal, octagonal, or any other shape across which fabric 102 may be stretched taut when frame 108 is in an uncompressed state. A circular-like shape was chosen for the illustrative embodiment herein as the shape is visually pleasing and when frame 108 is in a compressed state, for example, the volume and shape of surface 100 in the compressed state is approximately similar the uncompressed state, however the size is substantially reduced. In this example, the circular surface 100 in a compressed state can fit into a circular textile, zippered case which has the same circular shape, but is approximately one-quarter to one-half of the overall size of the surface 100 in an uncompressed state.

Lastly, as illustrated in FIG. 1, handle 110 is located on compressible frame 108 such that a user can hold compressible frame 108 and not interfere with fabric 102 affixed to said frame 108. Handle 110 is illustrated in FIG. 1 as being a grip-like structure which substantially conforms to the shape of compressible frame 108. However, a variety of shapes, sizes and materials are contemplated for handle 110. Handle 110 can be manufactured of the same, substantially similar, or different material than frame 108. For example, handle 110 can be a compressible foam-like material, a composite material, a textile material, a plastic, and/or a metal. Furthermore, handle 110, may also be formed of a material with a high tactile strength, such as wood or ceramic for a visually pleasing effect, if manufactured in such a way as to not interfere otherwise with the overall integrity and function of surface 100, fabric 102 and frame 108.

When a user, for example, an insurance claims investigator or claims adjuster, is holding handle 110 of the uncompressed frame 108 at an angle between 0° and 180°, the user can reflect radiant energy (not shown) through the fabric onto a vehicle body and create a whorl reflection pattern of at least one stripe of a dark color parallel to at least one stripe of a light color on the impression in the vehicle body to maximize viewing of the impression by the user. Radiant energy and the functional importance of the whorl pattern as it specifically relates to review of vehicle body surface for insurance claims purposes is discussed in more detail below, in reference to FIG. 2.

Figure 2:
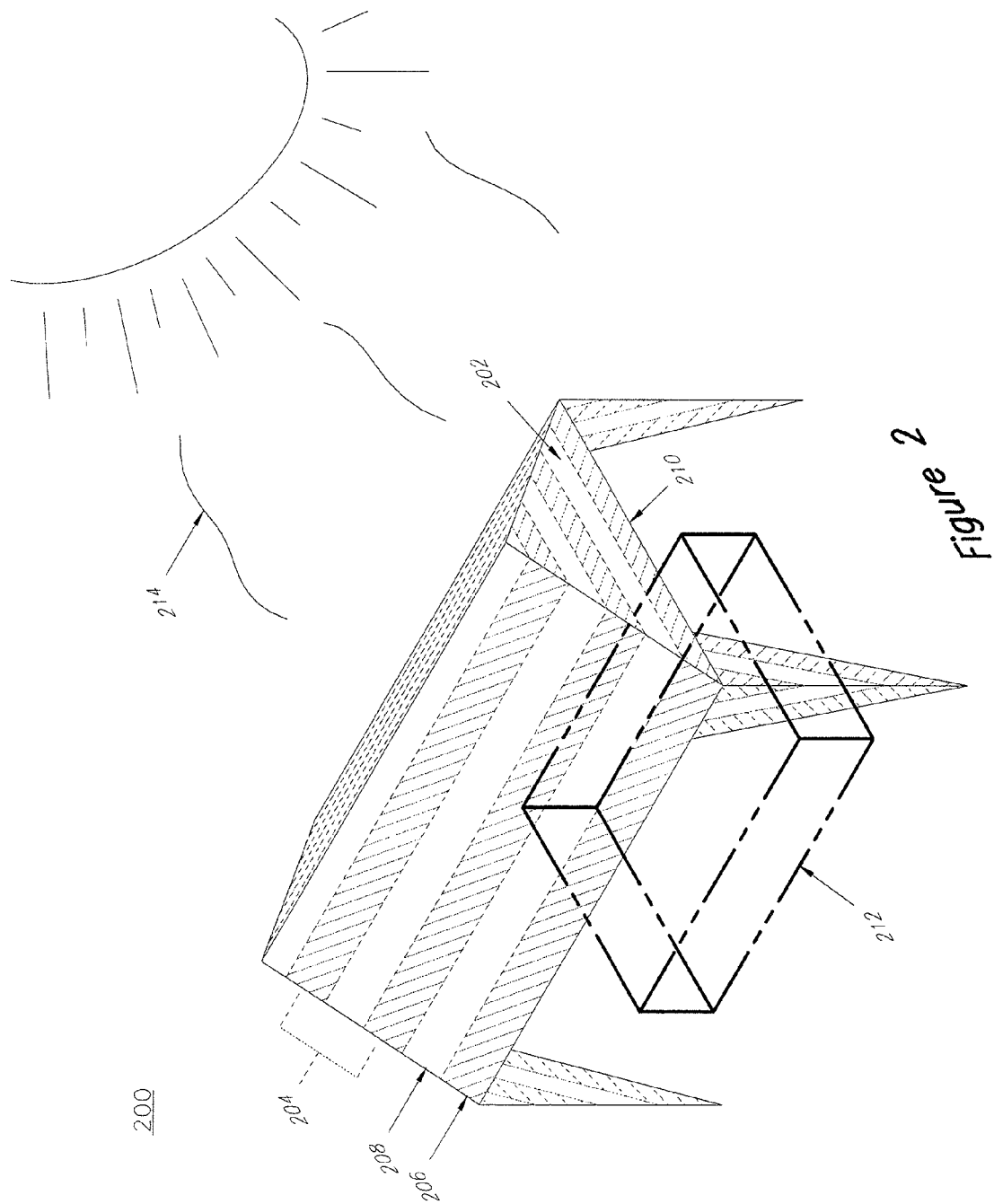
FIG. 2 illustrates one exemplary embodiment of a fabric mirror to maximize the viewing of an impression in a vehicle body, generally comprising a woven cloth and a frame.

FIG. 2 illustrates a second embodiment of the present invention, a fabric mirror 200, to maximize the viewing of an impression in a vehicle body 212. As shown in FIG. 2, fabric mirror 200 can further comprise a woven cloth 202 and a frame 210 to which the woven cloth 202 is affixed.

A mirror can be defined as something that shows what another thing is a very clear and accurate way, in one example, a polished or smooth surface that forms images by reflection. Furthermore, mirrors may be defined as objects that give a true representation. This relationship of an object to its mirror image can be more specifically defined as the relationship exhibited by two similar but non-superimposable crystal or molecular structures. A mirror image is a reflected duplication of an object that appears identical but reversed. As an optical effect, a mirror image results from reflection off of substances such as a mirrored glass, a metallic surface, and/or water. A mirror image is also a concept in geometry and can be used as a conceptualization process for three-dimensional structures.

The mirror image of an object or two-dimensional figure can be defined as the virtual image formed by reflection in a plane mirror. This may be conceptually visualized where the object is of the same size as the original object, yet different, unless the object or figure has reflection symmetry, which may also be known as P-symmetry.

Two-dimensional mirror images can be seen in the reflections of mirrors or other reflecting surfaces, or on a printed surface seen inside out. A mirror, for example, may not just produce an image of what would be there without it; it also changes the light distribution in the halfspace in front of and behind the mirror. A glass mirror hanging on the wall makes the room brighter because additional light sources appear in the mirror image. However, the appearance of additional light does not violate the conservation of energy laws, as some light is missing behind the mirror as the mirror simply re-directs the light energy.

In terms of the light distribution, the virtual mirror image has the same appearance and the same effect as a real, symmetrically arranged half-space behind a window (instead of the mirror). Shadows may extend from the mirror into the halfspace before it, and vice versa. In the case of two mirrors, in planes at an angle α, looking through both from the sector which is the intersection of the two halfspaces, is like looking at a version of the world rotated by an angle of 2α; the points of observations and directions of looking for which this applies correspond to those for looking through a frame like that of the first mirror, and a frame at the mirror image with respect to the first plane, of the second mirror. If the mirrors have vertical edges then the left edge of the field of view is the plane through the right edge of the first mirror and the edge of the second mirror which is on the right when looked at directly, but on the left in the mirror image.

In the case of two parallel mirrors, looking through both once is like looking at a version of the world which is translated by twice the distance between the mirrors, in the direction perpendicular to them, away from the observer. Since the plane of the mirror in which one looks directly is beyond that of the other mirror, one always looks at an oblique angle, and the translation just mentioned has not only a component away from the observer, but also one in a perpendicular direction. The translated view can also be described by a translation of the observer in opposite direction. For example, with a vertical periscope, the shift of the world is away from the observer and down, both by the length of the periscope, but it is more practical to consider the equivalent shift of the observer: up, and backward. It is also possible to create a non-reversing mirror by placing two first surface mirrors at 90° to give an image which is not reversed.

As illustrated in FIG. 2, fabric mirror 200 includes woven cloth 202, which is defined in more detail above, with reference to FIG. 1, further comprises a pattern 204 of at least one set stripe of a dark color 206 and at least one stripe of a light color 208. Pattern 204 is illustrated in FIG. 2 as stripes of similar width and dimension, however, it is contemplated that pattern 204 include any pattern which is functionally compatible with the intended inventive concept. For example, a pattern can generally be defined as a readily discernable regularity of elements. Therefore, pattern 204 can have any discernable regularity, including, but not limited to, symmetries, trees and other structures with a fractal dimension, spirals, meanders, waves, foams, tilings, cracks, spots and non-symmetrical stripes.

In additional embodiments as reasonably contemplated in view of illustrated FIG. 2, optional properties which may be functionally compatible elements of the inventive concept can include, but are not included to woven cloth 202 optionally having a translucency between 3 deniers and 90 deniers, or a translucency between 20 deniers and 60 deniers.

Additionally, pattern 204 can consist of more than one stripe of a dark color 206 and more than one stripe of a light color 208, creating an alternating pattern 204 of stripes. Furthermore, pattern 204 can include at least one set stripe of a dark color 206 and at least one stripe of a light color 208 where the stripes are of equal width. Optionally, pattern 204 can include at least one set stripe of a dark color 206 and at least one stripe of a light color 208 where the stripes are of unequal width.

As further illustrated in FIG. 2, when woven cloth 202 is affixed to frame 210, woven cloth 202 is taut. However, additional embodiments contemplate where woven cloth 202 when affixed to frame 210 is slack or non-taut. These embodiments, though not optimal when fabric mirror 200 is in use with certain types of vehicle bodies, may be necessary and functionally optimal depending on the material used to fabricate and/or manufacture the vehicle body to be viewed.

As is shown in FIG. 2, frame 210 can be a tent or awning structure through which a vehicle comprising the vehicle body can drive, so that the vehicle can me moved dependent upon the source of radiant energy, as discussed below. However, it is contemplated in additional embodiments of the present invention that frame 210 can have any configuration necessary so as to optimally maximize viewing of impressions in a vehicle body. For example, where the vehicle is an airplane, ship, boat, submarine, automobile, bicycle, motorcycle, or other mechanical motorized and/or non-motorized vehicle, the shape of frame 210 may be altered to be substantially similar in shape and size to the specific vehicle. Additional embodiments further contemplate where the shape of frame 210 may be altered so as to be substantially un-similar in shape and size to the specific vehicle, but to be formed, fabricated and/or manufactured in such a way so as to maximize viewing dependent on multiple varieties of radiant energy.

As illustrated in FIG. 2, when a vehicle body 212 is placed beneath frame 210, radiant energy 214 passes through woven cloth 202 onto vehicle body 212 and a reflection of the pattern 204 of at least one set stripe of a dark color 206 and at least one stripe of a light color 208 is reflected on any impression in the vehicle body 212 as a whorl pattern (not shown), to maximize viewing of the impression by a user.

Reflection, as briefly described above, can be defined as the change in direction of a wavefront at an interface between two different media so that the wavefront returns into the medium from which it originated. Common examples include, but are not limited to, the reflection of light, sound and water waves. The law of reflection says that for specular reflection the angle at which the wave is incident on the surface equals the angle at which it is reflected. For example, any type of mirror exhibits specular reflection.

In other examples of reflection, for example, in acoustics, reflection causes echoes and is used in sonar. In geology, it is important in the study of seismic waves. Reflection can be observed with surface waves in bodies of water. Reflection can be observed with many types of electromagnetic wave, besides visible light. In one example, reflection of VHF and higher frequencies is important for radio transmission and for radar. Even hard X-rays and gamma rays can be reflected at shallow angles with special "grazing" mirrors.

One example of radiant energy contemplated by the current embodiment, and as illustrated in FIG. 2 is sunlight. Sunlight can be defined as a portion of the electromagnetic radiation given off by the Sun, in particular infrared, visible, and ultraviolet light. Generally, on Earth, sunlight is filtered through the Earth's atmosphere, and is obvious as daylight when the Sun is above the horizon. When the direct solar radiation is not blocked by clouds, it is experienced as sunshine, a combination of bright light and radiant heat. When it is blocked by the clouds or reflects off other objects, it is experienced as diffused light. Fabric mirror 200 as illustrated in FIG. 2 is contemplated to be optimally functional in sunshine, bright light, and diffused light. In additional embodiments of the present invention, fabric mirror 200 is also contemplated to work in direct artificial lighting settings. However, fabric mirror 200 is not contemplated to be used in instances of "radiant heat" only.

In terms of energy, sunlight at the earth's surface is around 52 or 55 percent infrared (above 700 nm), 43 or 42 percent visible (400 to 700 nm), and 5 or 3 percent ultraviolet (below 400 nm). At the top of the atmosphere sunlight is about 30% more intense, having about 8% ultraviolet (UV), with most of the extra UV consisting of biologically-damaging shortwave ultraviolet. Radiant flux or radiant power is the measure of the total power of electromagnetic radiation (including infrared, ultraviolet, and visible light). The power may be the total emitted from a source, or the total landing on a particular surface.

Direct sunlight has a luminous efficacy of about 93 lumens per watt of radiant flux, higher than most artificial lighting, including fluorescent. Multiplying the figure of 1050 watts per square meter by 93 lumens per watt indicates that bright sunlight provides an illuminance of approximately 98 000 lux (lumens per square meter) on a perpendicular surface at sea level. The illumination of a horizontal surface will be considerably less than this if the sun is not very high in the sky. Averaged over a day, the highest amount of sunlight on a horizontal surface occurs in January at the South Pole.

Light scattering, as illustratively depicted in FIG. 2, is a form of scattering in which light is the form of propagating energy which is scattered. Light scattering can be thought of as the deflection of a ray from a straight path, for example by irregularities in the propagation medium, particles, or in the interface between two media. Deviations from the law of reflection due to irregularities on a surface are also usually considered to be a form of scattering. When these irregularities are considered to be random and dense enough that their individual effects average out, this kind of scattered reflection is commonly referred to as diffuse reflection.

Most objects that one generally sees are visible due to light scattering from their surfaces. Indeed, this is our primary mechanism of physical observation. Scattering of light depends on the wavelength or frequency of the light being scattered. Since visible light has wavelength on the order of a micrometer, objects much smaller than this cannot be seen, even with the aid of a microscope. For example, colloidal particles as small as 1 μm have been observed directly in aqueous suspension.

The transmission of various frequencies of light is essential for applications ranging from window glass to fiber optic transmission cables and infrared (IR), heat-seeking missile detection systems. Light propagating through an optical system can be attenuated by absorption, reflection and scattering.

Spectroscopy is the study of the interaction between matter and radiated energy, such as radiant power from direct sunshine, bright light and diffused light. Historically, spectroscopy originated through the study of visible light dispersed according to its wavelength, by a prism. Later the concept was expanded greatly to comprise any interaction with radiative energy as a function of its wavelength or frequency.

Spectroscopic data is often represented by a spectrum, a plot of the response of interest as a function of wavelength or frequency. The watt (W), the fundamental unit of optical power, is defined as a rate of energy of one joule (J) per second. Optical power is a function of both the number of photons and the wavelength. Each photon carries an energy that is described by Planck's equation: $Q=hc/l$, where $Q$ is the photon energy (joules), h is Planck's constant ($6.623 \times 10^{-34}$ J s), c is the speed of light ($2.998 \times 10^8$ m s-1), and $\lambda$ is the wavelength of radiation (meters). All light measurement units are spectral, spatial, or temporal distributions of optical energy. Yellowish-green light receives the greatest weight because it stimulates the eye more than blue or red light of equal radiometric power: 1 watt at 555 nm=683.0 lumens.

To perceptively illustrate this measurement, the human eye can detect a flux of about 10 photons per second at a wavelength of 555 nm. This corresponds to a radiant power of $3.58 \times 10^{-18}$ W (or J s-1). Similarly, the eye can detect a minimum flux of 214 and 126 photons per second at 450 and 650 nm, respectively. Effective irradiance is weighted in proportion to the biological or chemical effect that light has on a substance. A detector and filter designed with a weighted responsivity will yield measurements that directly reflect the overall effect of an exposure, regardless of the light source.

As discussed above with respect to both FIGS. 1 and 2, light reflecting off of a polished or mirrored surface obeys the law of reflection: the angle between the incident ray and the normal to the surface is equal to the angle between the reflected ray and the normal. Precision optical systems use first surface mirrors that are aluminized on the outer surface to avoid refraction, absorption, and scatter from light passing through the transparent substrate found in second surface mirrors. When light obeys the law of reflection, it is termed a specular reflection. Most hard polished (shiny) surfaces are primarily specular in nature. Even transparent glass specularly reflects a portion of incoming light. Diffuse reflection is typical of particulate substances like powders. If a light is shown on baking flour, for example, a directionally shiny component will not be seen. The powder will appear uniformly bright from every direction. Many reflections are a combination of both diffuse and specular components. One manifestation of this is a spread reflection, which has a dominant directional component that is partially diffused by surface irregularities.

When light passes between dissimilar materials, the rays bend and change velocity slightly, an effect called refraction. Refraction is dependent on two factors: the incident angle, θ, and the refractive index, n of the material, as given by Snell's law of refraction: n sin(q)=n' sin(q'). For a typical air-glass boundary, (air n=1, glass n'=1.5), a light ray entering the glass at 30° from normal travels through the glass at 19.5° and straightens out to 30° when it exits out the parallel side. The index of refraction itself is also dependent on wavelength. This angular dispersion causes blue light to refract more than red, causing rainbows and allowing prisms to separate the spectrum.

Generally it is necessary to diffuse light, either through transmission or reflection. Diffuse transmission can be accomplished by transmitting light through roughened quartz, flashed opal, or polytetrafluoroethylene (PTFE, Teflon). Diffusion can vary with wavelength. Teflon is a poor IR diffuser, but makes an excellent visible/UV diffuser. Quartz is required for UV diffusion. Integrating spheres are coated with BaSO4 or PTFE, which offer >97% reflectance over a broad spectral range with near perfect diffusion. These coatings are, however, quite expensive and fragile. When light reflects off of a rear surface mirror, the light first passes through the glass substrate, resulting in reflection losses, secondary reflections, and a change in apparent distance. First surface mirrors avoid this by aluminizing the front, and coating it with a thin protective SiO coating to prevent oxidation and scratching. Concave mirrors are often used to focus light in place of a lens. Just as with a lens, a concave mirror has a principal focus, f, through which all rays parallel to the optical axis pass through. The focal length of a spherical concave mirror is one half the radius of the spherical surface. Reflective systems avoid the chromatic aberrations that can result from the use of lenses.

The irradiance or illuminance falling on any surface varies as the cosine of the incident angle, θ. The perceived measurement area orthogonal to the incident flux is reduced at oblique angles, causing light to spread out over a wider area than it would if perpendicular to the measurement plane. To measure the amount of light falling on human skin, you need to mimic the skin's cosine response. Since filter rings restrict off-angle light, a cosine diffuser must be used to correct the spatial responsivity.

A Lambertian surface provides uniform diffusion of the incident radiation such that its radiance or luminance is the same in all directions from which it can be measured. Many diffuse surfaces are, in fact, Lambertian. The human eye, with its restricted solid viewing angle, is an ideal luminance, or brightness, detector. Since, by the cosine law, a radiance detector sees twice as much surface area in the same solid angle for the 60° case, the average incremental reflection must be half the magnitude of the reflection in the 0° case. A Lambertian surface that has a radiance of 1.0 W/cm2/sr will radiate a total of π*A watts, where A is the area of the surface, into a hemisphere of 2πste radians. Since the radiant exitance of the surface is equal to the total power divided by the total area, the radiant exitance is π W/cm2. In other words, if you were to illuminate a surface with an irradiance of 3.1416 W/cm2, then you will measure a radiance on that surface of 1.00 W/cm2/sr (if it is 100% reflective).

To effectively implement the maximization of viewing of an impression on a vehicle body 212 using fabric mirror 200, a number of interchangeable and optional steps are considered. For example, one step can include locating the vehicle body 212 beneath frame 210 in a location optionally dependent on a direction of radiant energy 214 passing through woven cloth 202. As discussed above, and inferred by the illustration in FIG. 2, radiant energy 214 can be sunlight, and vehicle body 212 can be driven and/or relocated to a specific location underneath of frame 210 depending on the time of day, the location of the sun, as well as based on other factors, including but not limited to, any precipitation, wind, buildings, non-building structures or the like.

Another optional step can include viewing a reflection of the woven cloth 202 on vehicle body 212 created by the directional radiant energy 214, whereby by the whorl pattern (not shown) is created by the pattern 204 of at least one set stripe of a dark color 206 and at least one stripe of a light color 208 to maximize, thereafter viewing of the impression by a user.

Figure 3:
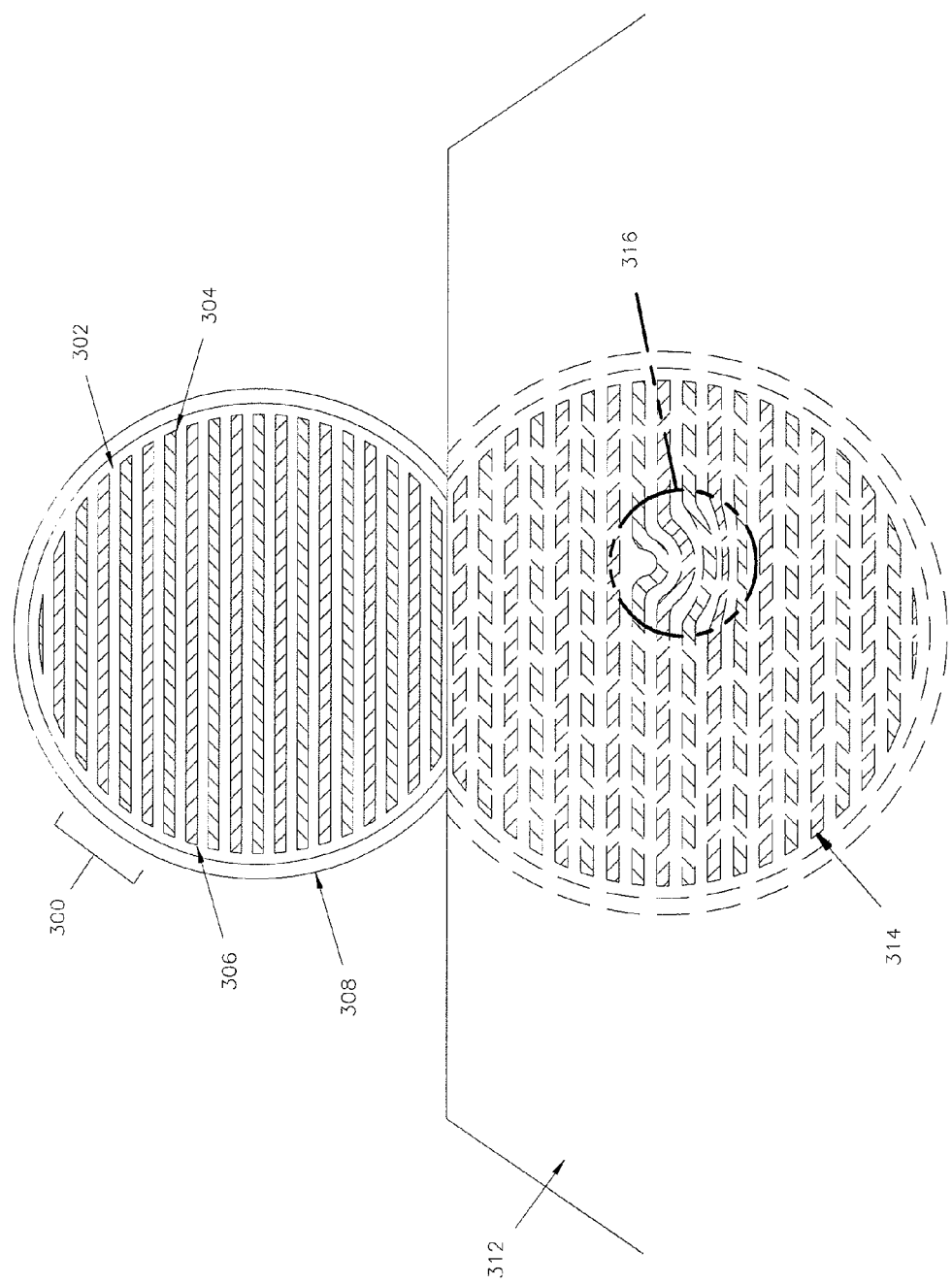
FIG. 3 illustrates one exemplary aspect of a surface to maximize the viewing of an impression in a vehicle body, generally a whorl pattern created by a reflection of the surface against the impression in the vehicle body.

FIG. 3 illustrates a reflection 314 of a fabric mirror 300 which creates a whorl pattern 316 on a vehicle body 312. Reflection 314 is created using fabric mirror 300, which comprises at least a fabric 302, at least one stripe of a dark color 304, at least one stripe of a light color 305, and a frame 308. Elements 300-308 are described in more detail above with reference to FIGS. 1 and 2.

As previously described, the irradiance or illuminance falling on any surface varies as the cosine of the incident angle, θ. A Lambertian surface, for example, vehicle body 312, can generally provide uniform diffusion of the incident radiation (not shown) such that its radiance or luminance is the same in all directions from which it can be measured. The human eye, with its restricted solid viewing angle, is an ideal luminance, or brightness, detector. A Lambertian surface that has a radiance of 1.0 W/cm2/sr will radiate a total of π*A watts, where A is the area of the surface, into a hemisphere of 2πste radians. Since the radiant exitance of the surface is equal to the total power divided by the total area, the radiant exitance is π W/cm2.

Therefore, if you were to illuminate a surface with an irradiance of 3.1416 W/cm2, then you will measure a radiance on that surface of 1.00 W/cm2/sr (if it is 100% reflective). Generally, a vehicle body 312, such as those illustrated in FIGS. 2 and 3, shall not have 100% reflectiveness because of a number of factors, including but not limited to, the material which body 312 is formed, fabricated and/or manufactured, paint and/or surface finish of the specific material. Another factor as to the reflectiveness of the material may also include the type of radiant energy present, i.e, full direct sunlight, artificial light, a combination thereof, or a form of ambient non-direct light.

Whorl pattern 316, as illustrated in FIG. 3, is depicted as a type of spiral also known as an expanding circular pattern. In botany, a whorl can be defined as an arrangement of sepals, petals, leaves, stipules, or branches that radiate from a single point and surround or wrap around the stem. In this context, a whorl consists of at least three elements, and it should be noted that a pair of opposite leaves is not called a whorl.

In biology, a whorl might occur at the ends of different structures or occur in the middle of structures. In this context, a whorl is often used to describe the structures of organs and used in the aid of identification, i.e. a cluster of cells or tissue that surround another, that starts at the same plain of axis or starts at one point and wraps around that point in an expanding circular pattern. Human fingerprints are commonly described as a whorl pattern.

As is described above, radiant energy passing through a translucent fabric 302, where fabric 302 has an alternating pattern of at least one stripe of a dark color 304 and at least one stripe of a light color 306, is diffused and scattered across a reflective surface such as vehicle body 312 which distorts the reflection 314 of the alternating pattern where there is an impression, indentation or wave in the vehicle body 312, thereby producing whorl pattern 316 which can be seen by the human eye. The whorl pattern 316 can be most beneficial where the damage is slight, for example, hail damage, sleet damage or minor dings and dents caused by slow-speed, low impact collision with an animate and/or inanimate object.

Insurance claims investigation is a very difficult and fact specific process, one in which assistance of an easily portable device to assist with viewing damage with the naked human eye is beneficial. One instance where such device would be beneficial is where an insurance adjust is required to adjudge hail damage on-site at a customer's home. Generally, one of the first steps in assessing this type of vehicle damage is to obtain background information from an owner of the vehicle as to when and where the vehicle was located at the time it was impacted. Additional information is also important, for example, weather records for the incident time and location, including publicly reported facts about hail size and storm direction, and assess the vehicle damage in light of that information. Another important step can include inspecting the vehicle at the incident location to confirm whether any environmental factors such as trees, buildings, or other obstructions could have shielded the vehicle and affected the distribution of the dents. Other necessary information to this type of review may include accounting for exterior characteristics, such as composite or aluminum body panels and other critical trim pieces.

Commonly, before an inspection for hail damage is conducted, the vehicles body 312 surface must be cleaned.

Generally, if the vehicle is not clean, it must be washed to ensure that all dents are observed and that the subtle details of each dent will not be obscured. Fabric mirror 300 may alleviate the necessity of on-site cleaning of a vehicle, and may allow for an inspector and/or investigator to easily closely examine each dent panel-by-panel, and number and list its characteristics.

Any form of impression, including but not limited to, dents, dings, creases or scratches would be easily ascertainable. Furthermore, the whorl pattern 316 reflection 314 may further allow for an investigator to fully determine whether any impacts have a half moon shape, round bottom, and consistent size, as well as any other distinguishing characteristics. Generally, a final step in hail damage investigation includes an investigator mark dents with contrasting-colored tape placed adjacent to the dent, using various colors to differentiate types of dents, e.g., blue for dents with typical creases, white for dents with scratches in the dent center.

Figure 4:
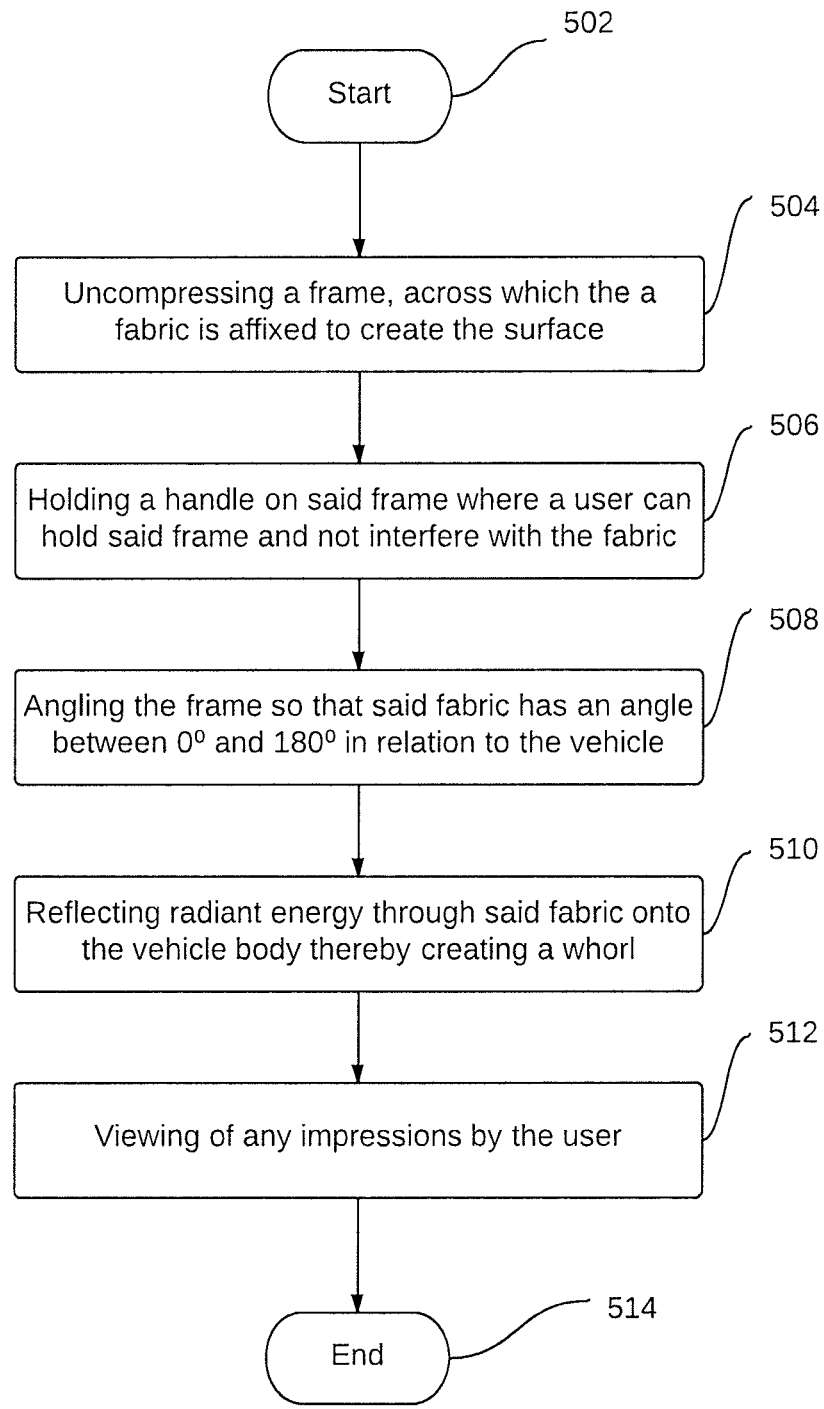
FIG. 4 illustrates one exemplary method for using a surface to maximize the viewing of an impression in a vehicle body.

FIG. 4 illustrates a logical flow diagram of one method 500 of using a fabric mirror and/or surface as embodied above in FIGS. 1-3. This method is provided as only one non-limiting option for operating the above described embodiments to maximize the viewing of an impression in a vehicle body.

At 502, the method begins where a user at 504 decompresses the frame, across which the fabric is affixed to create the surface. As noted above, when the frame is uncompressed the fabric is stretched taut across the frame and when the frame is compressed the fabric is slack across the frame. Furthermore, the fabric can have an alternating pattern of at least one stripe of a dark color parallel to at least one stripe of a light color.

Further embodiments contemplate where the fabric has a translucency between 3 deniers and 90 deniers, or where the fabric has a translucency between 20 deniers and 60 deniers. Also, additional embodiments contemplate where the fabric has more than one at least one stripe of a dark color parallel to at least one stripe of a light color creating an alternating pattern, the at least one stripe of a dark color has an equal width to the at least one stripe of a light color, or the at least one stripe of a dark color has an unequal width to the at least one stripe of a light color.

At 506, a user holds the handle on the frame, where the handle is located on the frame in such a manner so as to not interfere with the fabric affixed to said frame.

At 508, a user angles the frame so that said fabric has an angle between 0° and 180° in relation to the vehicle body. The angle at which the user optimally holds the frame is dependent on a number of factors as discussed above, including but not limited, to the type of radiant energy present, for example, sunlight, artificial light, diffuse light, or a combination thereof; the type of material of the vehicle body and the translucency and pattern on the fabric, and the like.

At 510, the radiant energy is reflected through the fabric onto and off of the vehicle body thereby creating a whorl reflection pattern of at least one stripe of a dark color parallel to at least one stripe of a light color on the impression in the vehicle body. The whorl pattern can be viewed by the naked human eye to optimize viewing by, for example, an insurance claims adjuster on-site at location where a vehicle has been damaged by inclement weather such as hail.

Lastly, at 512, the user views any impressions located on the vehicle body and determines the amount and extent of damage thereto.

The method thereafter ends at 514.

Additional methods, aspects and elements of the present inventive concept are contemplated in use in conjunction with individually or in any combination thereof which will create a reasonably functional method and device to be of use as fabric mirror and/or surface for maximizing the viewing of impression on a vehicle body. It will be apparent to one of ordinary skill in the art that the manner of making and using the claimed invention has been adequately disclosed in the above-written description of the exemplary embodiments and aspects. It should be understood, however, that the invention is not necessarily limited to the specific embodiments, aspects, arrangement and components shown and described above, but may be susceptible to numerous variations within the scope of the invention.

Moreover, particular exemplary features described herein in conjunction with specific embodiments and/or aspects of the present invention are to be construed as applicable to any embodiment described within, enabled thereby, or apparent wherefrom. Thus, the specification and drawings are to be regarded in a broad, illustrative, and enabling sense, rather than a restrictive one.

Further, it will be understood that the above description of the embodiments of the present invention are susceptible to various modifications, changes, and adaptations, and the same are intended to be comprehended within the meaning and range of equivalents of the appended claims.

What is claimed is:

1. A method of operating a surface to maximize the viewing of an impression in a vehicle body, comprising:
   uncompressing a frame, across which the a fabric is affixed to create the surface, wherein when the frame is uncompressed the said fabric is stretched taut across the frame and wherein when the frame is compressed the said fabric is slack across the frame, and wherein said fabric has an alternating pattern of at least one stripe of a dark color parallel to at least one stripe of a light color;
   holding a handle on said frame where a user can hold said frame and not interfere with the fabric affixed to said frame;
   angling the frame so that said fabric has an angle between 0° and 180° in relation to the vehicle body;
   reflecting radiant energy through said fabric onto the vehicle body thereby creating a whorl reflection pattern of at least one stripe of a dark color parallel to at least one stripe of a light color on the impression in the vehicle body; and
   viewing of said impression by the user.

2. The method of claim 1, wherein the fabric has a translucency between 3 deniers and 90 deniers.

3. The method of claim 1, wherein the fabric has a translucency between 20 deniers and 60 deniers.

4. The method of claim 1, wherein the fabric has more than one at least one stripe of a dark color parallel to at least one stripe of a light color creating an alternating pattern.

5. The method of claim 1, wherein the at least one stripe of a dark color has an equal width to the at least one stripe of a light color.

6. The method of claim 1, wherein the at least one stripe of a dark color has an unequal width to the at least one stripe of a light color.

7. A method of using the fabric mirror of claim 1, comprising:
   locating the vehicle beneath said frame to a location dependent on a direction of radiant energy passing through the woven cloth of the fabric mirror;

viewing a reflection of the woven cloth of the fabric mirror on the vehicle body created by the directional radiant energy, whereby by the whorl pattern is created by the pattern of at least one set stripe of a dark color and at least one stripe of a light color to maximize; and viewing of the impression by a user.

* * * * *